US010610115B1

(12) United States Patent
Zapesochny et al.

(10) Patent No.: US 10,610,115 B1
(45) Date of Patent: Apr. 7, 2020

(54) METHODS AND SYSTEMS FOR THE DELIVERY OF ACCURATE AND PRECISE MEASUREMENTS FROM THE BODY-SURFACE ELECTROCARDIOGRAM

(71) Applicant: eResearchTechnology, Inc., Philadelphia, PA (US)

(72) Inventors: Alexander Zapesochny, Rochester, NY (US); Jean-Philippe Y. Couderc, Rochester, NY (US); Thuan G. Pham, Rochester, NY (US); Mark L. Ticktin, Collegeville, PA (US); Randolph F. Brown, IV, Auburn, NY (US)

(73) Assignee: eResearch Technology, Inc., Philadelphia, PA (US)

( * ) Notice: Subject to any disclaimer, the term of this patent is extended or adjusted under 35 U.S.C. 154(b) by 132 days.

(21) Appl. No.: 15/604,368

(22) Filed: May 24, 2017

(51) Int. Cl.
*A61B 5/04* (2006.01)
*A61B 5/00* (2006.01)
*A61B 5/0402* (2006.01)

(52) U.S. Cl.
CPC ........ *A61B 5/04012* (2013.01); *A61B 5/0402* (2013.01); *A61B 5/7203* (2013.01); *A61B 5/7221* (2013.01)

(58) Field of Classification Search
CPC . A61B 5/04012; A61B 5/0402; A61B 5/7203; A61B 5/7221
See application file for complete search history.

(56) References Cited

U.S. PATENT DOCUMENTS

| | | | |
|---|---|---|---|
| 7,463,921 B2 | 12/2008 | Couderc et al. | |
| 7,912,535 B2 | 3/2011 | Couderc et al. | |
| 10,025,910 B2 | 7/2018 | Paty et al. | |
| 10,049,368 B2 | 8/2018 | Hansen et al. | |
| 2007/0055481 A1 | 3/2007 | Baird et al. | |

OTHER PUBLICATIONS

Co-pending U.S. Appl. No. 16/007,633, filed Jun. 13, 2018.
Co-pending U.S. Appl. No. 16/020,109, filed Jun. 27, 2018.
U.S. Appl. No. 15/291,103 Office Action dated Oct. 5, 2018.
U.S. Appl. No. 15/955,461 Office Action dated Aug. 9, 2018.

*Primary Examiner* — Lindsey G Wehrheim
(74) *Attorney, Agent, or Firm* — Wilson, Sonsini, Goodrich & Rosati, PC

(57) ABSTRACT

Described here are methods, devices, and systems for characterizing a physiological signal, and more specifically an electrocardiogram (ECG) signal. Generally, the method includes receiving an ECG signal generated by an ECG device coupled to a patient. The ECG signal may comprise a plurality of cardiac beat intervals. A set of evaluable replicates may be identified using a signal-to-noise ratio (SNR) for each cardiac beat, a repolarization signal, and an isoelectric line. Interval measurements may be determined from the set of evaluable multi-beat sequences. An ECG signal characteristic may be determined from the interval measurements.

28 Claims, 11 Drawing Sheets

METHODS AND SYSTEMS FOR THE DELIVERY OF ACCURATE AND PRECISE MEASUREMENTS FROM THE BODY-SURFACE ELECTROCARDIOGRAM

FIELD

Devices, systems, and methods herein relate to delivery of accurate and precise measurements of a physiological signal, specifically an electrocardiogram (ECG) signal.

BACKGROUND

Documented cases of fatal and non-fatal torsade de pointes (TdP), a type of lethal ventricular arrhythmia, associated with the use of new chemical entities (NCE) have resulted in the withdrawal of a number of drugs from the market. In further response to these public health concerns, the International Council for Harmonization Guidance (ICH E14) was implemented to guide drug developers in the conduct of thorough cardiac safety assessments on all NCEs and has since virtually eliminated post-market drug withdrawals due to arrhythmia and sudden cardiac deaths. Beginning from 2005, nearly all new compounds in development have been expected to undergo rigorous testing for their potential to prolong the QT interval (a surrogate marker of proarrhythmia) on an electrocardiogram (ECG).

New drugs seeking regulatory approval typically undergo systematic evaluation of the potential to cause QT prolongation in a Thorough QT (TQT) study, in healthy subjects or as part of an intensive assessment of ECGs collected from Phase I trials using exposure response modeling. One common challenge in conducting a TQT study or in assessing QT from Phase I data is obtaining and measuring ECG data that is reliable and that is measured with good precision. Even when QT/QTc interval measurements are made by an ECG core laboratory, poor precision can occur from a number of factors, including using too few beats from an ECG recording, resulting in sampling error, or that the cardiac beats being measured are too variable and were not representative of the time point from which they are taken. The variability may be increased due to poor signal quality and/or heart rate changes, for example. When poor precision occurs in a TQT or Phase I QT study, this generally results in wider confidence intervals in the study data. In a TQT study, if the lower-bounds of the wider confidence intervals fall below pre-specified thresholds in the positive control arm of a TQT study (the positive control arm is generally derived by having study subjects take the drug moxifloxacin), then regulators would generally conclude that assay sensitivity had not been achieved in the TQT study and that the results may be deemed to be inconclusive. Similarly, if the wider confidence intervals in a TQT or Phase I QT study caused any of the upper bounds of the confidence intervals from the drug arm(s) to cross a regulatory threshold of concern (typically a 10 ms change), then such drug may be viewed by one or more regulators as requiring further study relative to its QT effect and/or that such drug may require a cardiac safety warning label related to its potential to prolong QT. Therefore, it is important in TQT studies or Phase I QT studies that methodologies and measurement techniques and technologies resulting in highly precise ECG measurements be utilized. Additionally, TQT studies are often powered in terms of the number of subjects that are put into the study based on assumptions around the level of precision that can be achieved; therefore, better precision also enables a study to either be run with fewer subjects or to minimize the likelihood of inconclusive or false positive results.

Developing methodologies and technologies that help to identify and filter out the poor quality portions of ECG recordings and the signal intervals that contain non-reliable values is valuable, because excluding this data may reduce the imprecision or otherwise improve the accuracy of the ECG interval measurements as to the current state of the subject. Additionally, another challenge in TQT and Phase I QT studies stems from the somewhat subjective nature of determining the end of a T-wave, which is used to determine a QT value. Human experts that have been highly trained in measuring ECGs have nonetheless been shown in numerous studies to be inconsistent with their fellow experts as well as to even be inconsistent with themselves over time. This is why the E14 cardiac safety guidance for conducting a TQT recommends that ECG labs conduct an "inter- and intra-reader variability" assessment as part of any TQT study so that the amount of such inconsistency and variability due to human measurement can be known. Therefore, methodologies and systems that seek to offer optimal study precision also provide a benefit by minimizing variability introduced or caused by inconsistent human measurement expertise.

BRIEF SUMMARY

Described here are devices and methods for characterizing an ECG signal. In general, methods for characterizing an electrocardiogram (ECG) signal may comprise receiving an ECG signal or completed recording generated by an ECG device coupled to a patient or subject. The entire ECG recording, or a selected epoch from the entire ECG may be used for the analysis. The duration of an epoch may be specified by the protocol or industry standards, and is typically around a 5-minute ECG recording segment, or longer, and representative of a time point of that enrolled individual in a clinical study (e.g., control phase, washout phase, post-treatment time point, etc.). Individual cardiac beats and smaller consecutive sets or segments of beats may be analyzed based on a signal-to-noise ratio (SNR) computed from a repolarization signal and an isoelectric line. In some examples, a specified group or number of consecutive beats (e.g., a multi-beat sequence of three consecutive beats) may be analyzed sequentially or in an overlapping fashion, using the SNR of the sequence within the full ECG tracing, to identify longer segments of similar consecutive beats. These sequences or replicates may be specified with a fixed duration or beats (e.g., in the range of three to ten beats) or a minimum duration or number of beats (e.g., 10 seconds or longer) and would include one or more of sequential or non-overlapping multi-beat sequences. In a stable, high quality ECG recording, the replicate may comprise nearly entire epoch or full ECG. The identifier information and/or associated ECG parameters may be used to visually or digitally annotate the full ECG tracing, or may be used by a viewing program to select sequences within full or raw ECG tracing for display and analysis by a reviewer or technician. A relative ranking of the sequences based upon the sequence length, dispersion, and/or deviation may be provided, which may facilitate efficient review. A set of interval measurements may be generated from the set of evaluable multi-beat sequences using the SNR. An ECG signal characteristic may be determined from the set of evaluable intervals. The determined ECG signal characteristic may be, for example, an interval measurement and used to determine cardiac safety data with a high level of both accuracy and drug effect with a high level of precision.

In some variations, the ECG signal or recording comprises an epoch and a set of replicates, where each replicate in the epoch containing a predetermined number of consecutive cardiac beats or pre-determined period of time. The set of evaluable multi-beat sequences may be determined for each replicate. In some variations, a method of characterizing an ECG signal may include receiving an ECG signal generated by an ECG device coupled to a subject. The ECG signal may comprise a plurality of cardiac beats. The method may include the steps of determining a signal-to-noise ratio (SNR) for each cardiac beat, a repolarization signal, and an isoelectric line. A set of evaluable multi-beat sequences may be identified using the SNR of each cardiac beat, wherein the sequences have a pre-determined length. Interval measurements may be determined from the set of evaluable multi-beat sequences.

In some variations, the repolarization signal corresponds to a T-wave voltage that terminates at the T-wave offset. The identified set of evaluable multi-beat sequences may exclude multi-beat sequences that include non-sinus origin. The SNR may be based upon a ratio of a root mean square voltage of a T-wave and a root man square voltage of an isoelectric region prior to Q-onset of a corresponding QRS complex to the T-wave. The pre-determined length may be a pre-determined set length or a pre-determined minimum length. In some of these variations, the length is a time duration or several cardiac beats.

In some variations, the SNR may be given by the equation $$SNR = 20 * \log\left(\frac{V_{rms}\text{signal}}{V_{rms}\text{noise}}\right) \text{ where } V_{rms} = \frac{1}{n}\sqrt{\sum_{i=1}^{n} (v_i)^2}$$

and n is a $V_{rms}$ interval and v is voltage. The $V_{rms}$ signal may be a root mean square voltage in the T-wave from a J-point until a 4/7RR point and $V_{rms}$ noise may be a root mean square voltage in an isoelectric region over a 40 ms interval prior to Q-onset.

In some variations, the set of evaluable multi-beat sequences may be determined based on beat characteristics comprising at least one of heart rate stability, non-sinus beat morphology and QTcF. In some of these variations, the heart rate stability may be based on a median RR value for a predetermined duration prior to each cardiac beat. The beat may be excluded from the set of evaluable multi-beat sequences when the current RR value is greater than 20% of the median RR value.

The method may include additional variations. In some variations, determining the set of evaluable multi-beat sequences may comprise determining an order of the multi-beat sequences in the ECG signal based on at least one of a number of beats within the multi-beat sequence, heart rate stability, non-sinus beat morphology, the SNR, and a QTcF. In some variations, the method may include selecting from a plurality of processing automation levels. The ECG signal characteristic may be determined based on the selected processing automation level. In some of these variations, selecting from the plurality of automation levels may include a highly automatic level, a semi-automatic level and a manual adjudication level. The semi-automatic level may include greater user input than the highly automatic level, and the manual adjudication level may require greater user input than the semi-automatic level. In some of these variations, the highly automatic level comprises classifying beats for one of automatic processing and human review. In some variations, selecting from the plurality of automation levels selects the semi-automatic level when at least three consecutive beats in at least two of three sequences of a pre-determined length in the set of multi-beat sequences are determined as satisfactory. In some of these variations, the manual adjudication level may comprise determining the interval measurements based on extraction of at least three consecutive beats with full fiducial correction.

In some variations, noise may be removed from the ECG signal by at least one of baseline removal and 60 Hz interference removal. In some variations, a consistency check of the ECG signal characteristic may be performed comprising at least one of a data sequence check, interval measurement comparison and time point check. In some variations, a set of the evaluable replicates may be selected for a QT evaluation with a new chemical entity. In some of these variations, the QT evaluation may be performed for a Thorough QT (TQT) study, an exploratory Investigation New Drug study, a First-In-Human study, a microdose study, phase I study, phase II study or a phase III study.

In some variations, determining the set of evaluable replicates may comprise providing in ascending order the replicates based on a number of beats within the interval including presence of unstable heart rate, presence of non-sinus beats, unavailability of SNR and QTcF or other QT values outside a pre-specified non-physiological range.

Also described here are systems for characterizing an electrocardiogram (ECG) signal. In general, the system may include a receiver to receive an ECG signal generated by an ECG device coupled to a patient, wherein the ECG signal comprises a plurality of consecutive cardiac beats. The system may further include a processor configured to determine a set of evaluable intervals based on a signal-to-noise ratio (SNR) comprising a repolarization signal and an isoelectric line, and determine an ECG signal characteristic from the set of evaluable multi-sequence beats.

Additional methods for characterizing an electrocardiogram (ECG) signal are described in general, the method may include the steps of receiving an ECG signal generated by an ECG device coupled to a subject. The ECG signal may comprise a plurality of consecutive cardiac beat sequences. A set of non-evaluable consecutive cardiac beat sequences may be determined based on the presence of a non-sinus beats, unstable heart rate, an unavailable signal-to-noise ratio (SNR) and QTcF. The set of non-evaluable intervals (e.g., replicates) from be excluded from QT evaluation.

The methods described herein may include other optional adjustments and/or checks. For example, noise may be removed from the ECG signal by one or more wandering baseline correction, electromyographic (EMG) activity correction, and $^{5}\%_{60}$ Hz interference removal. A consistency check of the ECG signal characteristic may be performed and comprise at least one of a data sequence check, interval measurement comparison, and epoch check.

DETAILED DESCRIPTION

Figure 1:
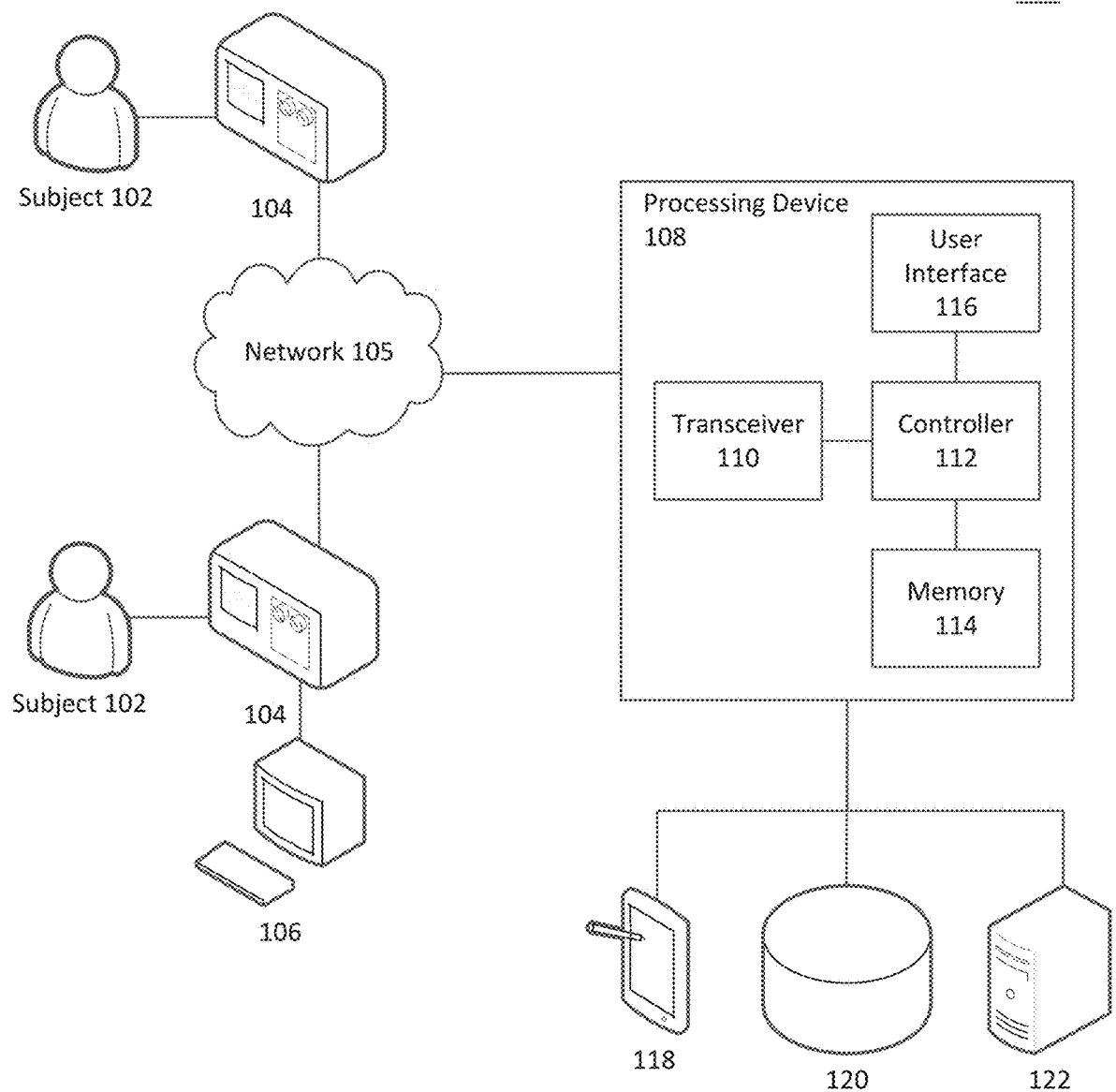
FIG. 1 depicts one variation of a system comprising an ECG device coupled to a patient.

Generally described here are devices, systems and methods for analyzing a physiological signal for monitoring at least one subject parameter. More particularly, described herein are devices, systems and methods for characterizing ECG signal quality. In some variations, the devices, systems, and methods described herein may identify a set of evaluable multi-beat sequences and determine interval measurements from the set of evaluable multi-beat sequences suitable for QT evaluation and analysis. The sequences may include the time durations of specific morphologies within a PAQRST complex, such as the PR, QT, and QRS intervals, or the time durations between two adjacent PQRST complexes, such as the RR interval. In another variation, the devices, systems, and methods described herein may provide a set of intervals that may be excluded from signal evaluation and analysis. The devices, systems and methods described herein may provide a set of sequences that may be used to determine a subject's participation in one or more clinical trials, from early to late stage studies such as Thorough QT studies, Phase I studies where QT is being assessed, and other studies where precision of ECG-based intervals are of particular concern or are part of the focus of a study.

Determination of ECG characteristics on a full set of raw ECG recordings generated by clinical trial studies may sometimes be unreliable as noise and a patient's physiological variability during ECG recording may result in inaccurate ECG interval measurements, which in some cases could lead to a subject's unnecessary exclusion from, or inappropriate inclusion, in an ECG study, and imprecise results.

By contrast, instead of analyzing the full ECG reading or recording, a set of consecutive multi-beat sequences, extracted from or otherwise identified in the full ECG reading, may be provided. Rather than providing a signal-averaged, or other artificially generated representative PQRST complex(es), a set of actual beat sequences of a pre-specified length or minimum length, or replicates, which are identified as suitable for QT evaluation and analysis are provided. This set of replicates may have a lower variability of heart rate, a low noise level, and/or comprise sinus beats relative to the full set of replicates or the full ECG reading. Deviations due to noise and other factors may be identified based on signal differences between replicates in the set to determine the similarity of the replicates to each other. The set of replicates having the lowest variability relative to the other replicates contain the least amount of noise and/or provide patient QT measurements with the highest accuracy and precision.

Prior to QT measurement and analysis, a set of high quality signal replicates are determined using an automated processing level determined based on the number and quality level of the signals available. Poor quality segments may be queued for potential exclusion, or automatically excluded from further processing to reduce the number of inconclusive, false positive and false negative results. In this manner, QT evaluation based on a high-quality set of evaluable ECG intervals having high accuracy and precision may improve the results of a cardiac safety study such as a TQT study while using less patients and may be applied to early stage clinical trials, where data is also being collected from fewer subjects than would typically be the case in a TQT study.

Importantly, consistent and reliable QT evaluation has been previously difficult in early stage clinical trials due to a lack of accuracy and precision. The devices, systems and methods described herein may be applied across a wide range of clinical trials, from early to late stage studies in order to gain early or more detailed insight into the cardiac safety profile of a drug. A significant proportion of traditional TQT studies have found that a therapeutic candidate or other biologically active agent to be potentially arrhythmia inducing, or that further detailed investigation of a drug's potential QT effect needs to occur. However, by accurately determining a cardiac safety profile in an early stage clinical trial, resources may be shifted away from high risk drugs before even more significant investment and development efforts are undertaken. Increased efficiency may also be realized if reliable cardiac safety data is generated from early stage studies that are routinely performed as part of the clinical development program. Thus, the early acquisition of reliable cardiac safety data significantly benefits the risk management of a drug development program.

Additionally, QT evaluation based on identified evaluable multi-beat sequences as described herein may be more accurate and precise, thus increasing confidence in subject recruitment decisions for a clinical trial. For instance, unnecessary patient exclusion related to falsely-elevated, imprecise ECG machine interpreted QT intervals may be minimized through analysis of high quality ECG signal segments. As a result, recruitment may be accelerated, resulting in an earlier database lock, leading to significant cost savings during phase II and III studies, for example.

In some variations, proarrhythmia risk may be assessed in First-in-Human (FIH) studies, such as single ascending dose (SAD) or multiple ascending dose (MAD) studies. The minimum number of subjects per cohort/dose groups in a FIE study may be six to nine subjects. Even though doses are distributed across several small cohorts, an intense ECG assessment schedule where such ECGs are assessed in a reliable and precise manner, and where such ECG data is subsequently analyzed using a statistical technique such as exposure response modeling, may provide cardiac safety data with at least the same level of confidence as a TQT study.

Accordingly, the cardiac risk assessment traditionally obtained in a TQT study may be achieved through robust ECG monitoring and exposure-response (ER) analysis of data generated from SAD and/or MAD studies. The cardiac safety assessment conducted in conjunction with an FIH study may be provided at a fraction of the cost of a TQT study that typically requires millions of dollars and a significant timeframe to plan and execute. In addition, earlier reliable assessment of cardiac safety data may altogether replace a late stage, resource intensive TQT study. This may significantly decrease the overall development cost and/or time to bring a new drug to market.

Figure 9:
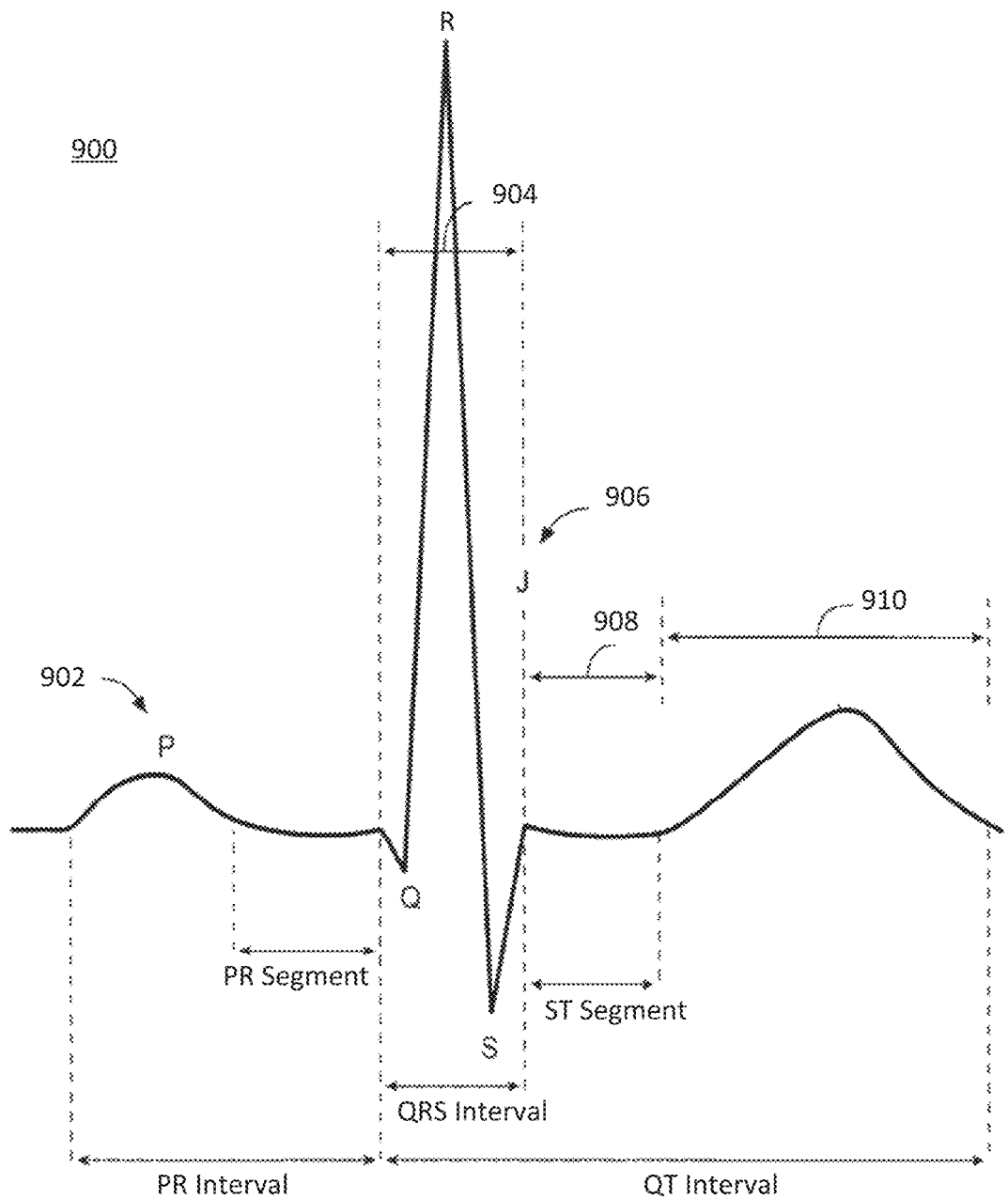
FIG. 9 is an illustrative ECG waveform of cardiac electrical activity.

FIG. 9 illustrates an exemplary ECG waveform (900) of normal cardiac electrical activity generated by an electrocardiograph device plotted as a function of voltage and time.

Initially, a P-wave (902) caused by atrial depolarization is observed having a relatively short duration rounded positive deflection. Subsequent to this, the Q-wave provides a small but sharp negative deflection, as a result of interventricular septal depolarization. Next, an R-wave includes a very large and sharp positive deflection resulting from ventricular depolarization, after which an S-wave provides a sharp and large negative deflection, which represents depolarization of the Purkinje fibers, after spreading through the ventricles from top to bottom, and then back up again. The presence of these deflections is not systematic and according to the angle of the recording QRS complex may have a more simple configuration such as QR or RS amongst others.

When the Q, R and S waves are taken together, they are known as the QRS complex (904). The QRS complex (904) is caused by ventricular depolarization. Depending upon the subject and/or the particular ECG lead being evaluated, not all of the components of the QRS complex (904) may be present, and the term may also be used to described, for example a QR or RS cardiac morphology, amongst others. The PR interval is measured from the beginning of the P-wave (902) to the beginning of the QRS complex. The QRS complex (904) ends at J-point (906). The J-point (906) is also the point at which the ST segment (908) begins, the ST segment (908) being associated with the ventricular being depolarized, and therefore should be isoelectric in normal cardiac tissue. The ST segment (908) is followed by a T-wave (910) that represents the repolarization of the ventricles. The JT peak interval is from the J point to the apex of the T-wave and represents a sub-interval of the QT interval. The QT interval is measured from the beginning of the QRS complex (904) to the end of the T-wave (910). Abnormalities in the QT interval (including the JT peak interval) often mark susceptibility to life-threatening arrhythmias as discussed above.

ECG parameters such as the QT interval, QRS complex (e.g., QRS onset, QRS offset), J point, T-wave (e.g., T-wave apex, T-wave endpoint), and other features may be determined from ECG signal data in a variety of ways. The devices, systems, and methods described herein may comprise one or more of the methods for detecting ECG parameters described in U.S. Pat. No. 7,463,921, filed on Aug. 13, 2002, and titled "METHOD AND SYSTEM FOR ANALYZING AN ELECTROCARDIOGRAPHIC SIGNAL," and/or U.S. Pat. No. 7,912,535, filed on Mar. 1, 2007, and titled "METHOD AND SYSTEM FOR ASSESSING REPOLARIZATION ABNORMALITIES," each of which is hereby incorporated by reference in its entirety. In some variations, a corrected QT interval may be calculated by using one or more Bazett, Fridericia, and Framingham corrections, given below:

$$Bazett\ QTc=QT*RR^{1/2}$$

$$Fridericia\ QTcF=QT*RR^{1/3}$$

$$Framingham\ QTc=QT+0.154+0.154*(1000-RR)$$

$$Nomogram\ QTc=QT+0.116*(1000-RR)\ if\ RR>1000,$$
$$or\ QT+0.156*(1000-RR)\ if\ 600<RR<1000,\ or$$
$$QT+0.384*(1000-RR)\ if\ RR<600$$

In other variations, an ECG signal quality processing device may be provided remotely relative to an ECG device connected to a subject. In this manner, clinical ECG devices may be utilized to record subject data without relying on the poor accuracy of their internal QT reading algorithms. This allows for faster and more consistent ECG analysis across different studies and locations.

I. Systems

Devices for characterizing an ECG signal generally include a receiver for receiving ECG signal data and a processor and memory for analyzing the received data to determine ECG signal data characteristics. The receiver may be configured to receive the ECG signal generated by an ECG device coupled to a patient. The processor may be configured to determine a set of evaluable interval measurements of the ECG signal. In some variations, evaluable interval measurements (e.g., multi-beat sequences) may be identified using an SNR of each cardiac beat. In some variations, the ECG signal data characteristic may be determined from evaluable interval measurements determined based on a signal-to-noise ratio (SNR). In another variation, the device may be provided remotely from the ECG device and the patient and communicate over a network. The processor may be further configured to provide the ECG signal data characteristic for QT evaluation associated with a new chemical entity.

Overview

FIG. 1 depicts one variation of a system (100) comprising a subject (102) coupled to an ECG device (104) at a patient or clinical study site. The patient site may further include an on-site computing device (106) configured to communicate with the processing device (108) and provide information to a user such as a subject (102), reviewer, ECG technician, and the like. The subject (102) may be connected to the ECG device (104) through a set of leads and generate ECG signal data received by the processing device (108) over a network (105) such as a wireline or wireless network. An output of the processing device (108) may be transmitted to one or more of the ECG device (104), computing device (106) and other computing devices (118, 120, 122) (e.g., database, server, and the like). Data transmission may be provided through Hyper Text Transfer Protocol Secure (HTTPS) or other data transmission protocol. Data may be encrypted on any of the devices described herein. For example, subject identifying information may be secured via unique user authentication and backed up according to HIPAA regulations.

In some variations, an ECG signal generated at the ECG device (104) may be transmitted to a centralized ECG laboratory including processing device (108) for processing and analysis, thus avoiding signal analysis performed by the ECG device (104) using its internal automated measurement algorithms, which may generate incorrect results or falsely elevated QTc readings. For example, centralized processing may improve study recruitment through more consistent and reliable analysis of ECG signal data. In some variations, the processing device (108) may be provided on-site with the subject (102), incorporated into an ECG device (104), and/or the computing device (106).

ECG Device

As discussed above, an ECG device (104) may be provided for ECG data collection and patient safety but need not be used to determine a final QT measurement. The ECG device (104) may record ECG signal data from a subject using a set of ECG leads coupled to the subject (102) at the ECG device (104). The number of ECG leads (not shown) and positioning of the leads used for ECG recording may vary, depending upon the clinical need. Examples of ECG lead systems include a standard 12-lead electrocardiogram (e.g., leads I, II, III, aVR, aVL, aVF, V1, V2, V3, V4, V5 and V6), Mason-Likar (upper body limb lead placement), and "Frank" electrode lead system (e.g., 7 electrodes), McFee-Parungao Lead System, 5-lead systems, 3-lead systems, and the like. Other examples include 3-lead systems, or the addition of right-sided precordial leads (V1R to V6R), posterior chest leads (V7 to V9), leads placed in higher or lower intercostal spaces, and the like.

The ECG signal data generated by ECG device (104) may be generated in any of the known digital ECG formats, or alternative image formats, such as .jpg, .gif, and the like. In some variations, ECG signal formats may include, but are not limited to, the Standard Communications Protocol for computer assisted ElectroCardiography (SCP-ECG), HL7 annotated ECG (HL7 aECG), Digital Imaging and Communication in Medicine (DICOM) Waveform Supplement 30 and Medical waveform Format Encording Rules (MFER). Any known digital ECG format may be utilized in conjunction with the devices and methods described herein.

In some variations, continuous ECG digital signal data recordings with high-resolution (e.g., 1000 Hz, 16-bit resolution or 500 Hz sampling rate and 12-bit amplitude resolution) acquired from a subject are received by the processing device (108). The ECG signal data may include a plurality of cardiac beats and corresponding time point (TP), an optional section of the ECG of a pre-specific length by time duration or number of beats (which may provide consistency of recording length), information which are relative time stamps at which drug concentration or other information relevant to the aim of a clinical study are measured. In other variations, the ECG signal data may be recorded at a rate in the range of about 125 Hz to about 250 Hz, about 500 Hz to about 1 kHz, and about 1 kHz to about 16 kHz with a resolution in the range of about 8 bit to about 64 bit, about 16 bit to about 32 bit, and about 24 bit.

ECG data signals generated by the ECG device (104) may be affected by noise from one or more different sources, including physiological and non-physiological sources. Examples of physiological noise include axis shift, biphasic QRS morphology and QRS amplitude variations. Non-physiological noise sources may include $^{50}/_{60}$ Hz electric power lines, electrode motion artifacts, myogram, and baseline wander. Noise in an ECG signal may cause two types of beat detection errors: A false positive (FP) occurs when a beat detection algorithm falsely generates a sense marker (i.e., an indication of a beat) when there is no QRS complex; a false negative (FN) occurs when a beat detection algorithm fails to detect the true QRS complex. The ECG device (104) may transmit one or more of the raw ECG signal data and/or filtered signal data having signal noise removed. The ECG device (104) may be coupled to one or more devices (e.g., on-site device (106), processing device (108), and the like) and/or networks (105) to communicate.

Processing Device

A controller (112) may be configured to perform processing of ECG data, such as determining ECG signal quality and interval measurements from a set of evaluable multi-beat sequences. For example, the processing device (108) processes the ECG signal data to determine a set of evaluable intervals and an ECG signal characteristic from the set of evaluable intervals. In some variations, the device (108) may receive ECG data from a plurality of ECG devices (104) through network (105). Accordingly, the device (108) may provide centralized data collection and standardized ECG signal processing across a plurality of study locations, subjects and throughout a timeline of a study. The device (108) may also allow an authorized user to easily access and review patient study results and perform additional analysis. For instance, different levels of patient results may be available to one or more sponsors and authorized internal and/or external users via a web-based interface. As another example, end-of-study reporting may be required by sponsors and/or some domestic or international regulatory agencies. Record keeping, security and consistency may thus be improved when data processing and data storage is centralized at a processing device (108). This also allows trained personnel such as cardiologists or ECG technicians that manually process and review ECG data to be provided access at a central location, further increasing efficiency and cost savings.

Figure 8:
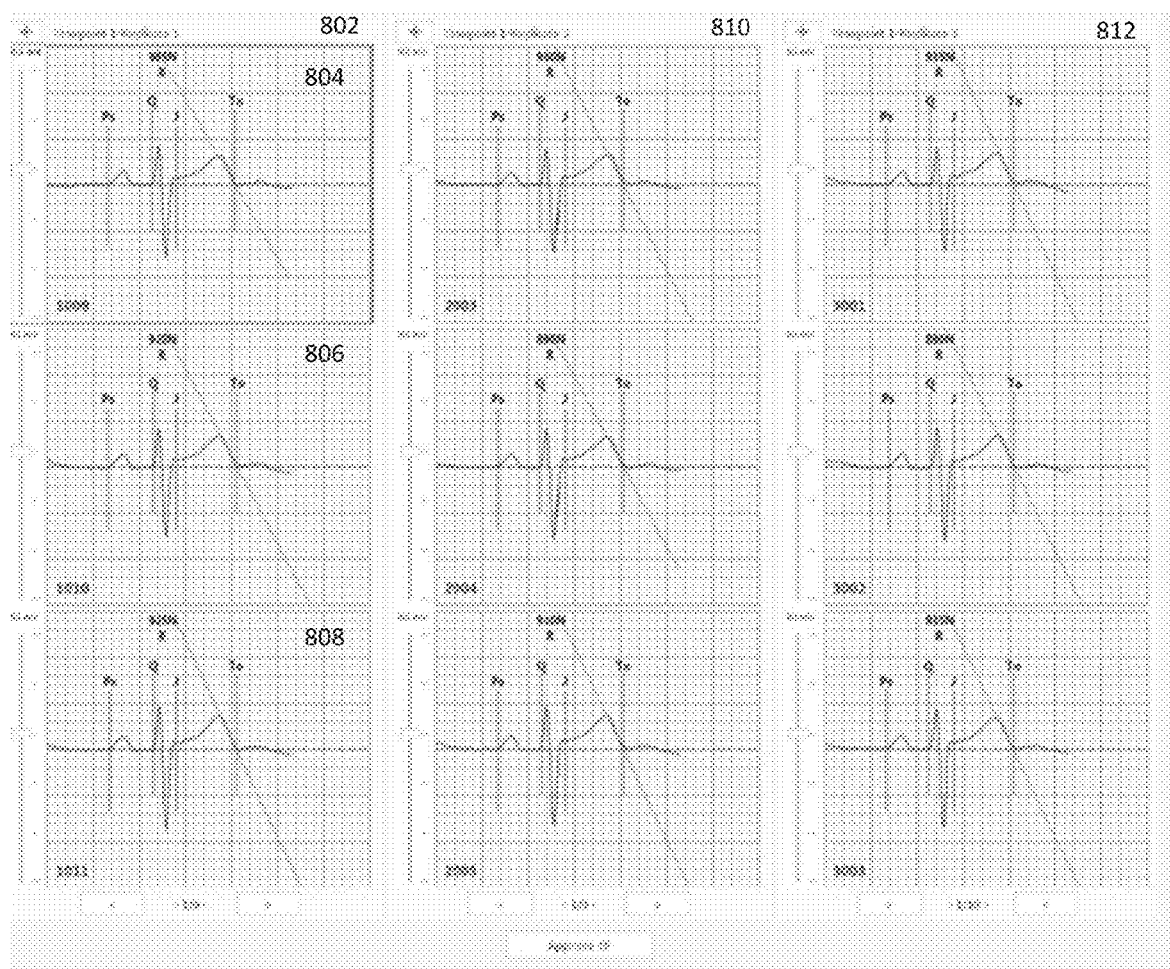
FIG. 8 depicts one variation of a graphical user interface of an ECG processing system.

The user interface (116) may comprise an input device and output device, including a display providing a user, such as a cardiologist, a set of evaluable intervals for analysis. FIG. 8 depicts one variation of a graphical user interface (GUI) (800) of an ECG device (104). In FIG. 8, a set of nine beats are displayed together on GUI (800) per time point. For instance, the three best beats (804, 806, 808) of a first replicate (802) are displayed in a column for analysis by a user. A second replicate (810) and third replicate (812) of the same time point may also be displayed adjacent to the first replicate (810). In this manner, a user may easily analyze an entire time point in one view to determine the highest quality beats to be measured for the time point. This is particularly advantageous over prior user interfaces that display only one to three beats on graphical user interface (GUI) per time point.

Once a network interface (110) receives ECG signal data generated by an ECG (104), the controller (112) of the processing device (108) may be configured to determine a set of evaluable multi-beat sequences and one or more ECG signal characteristics for each multi-beat sequence. The set of evaluable multi-beat sequences may be determined as described in further detail below. An ECG signal characteristic, including but not limited to the RR, PR, and QRS interval, may be determined from the set of evaluable multi-beat sequences. The QT evaluation may be performed using ECGs recorded from one or more of an animal study, a TQT study, a microdosing study, a First-In-Human study, a Phase I study, a Phase II study, and a Phase III study, for example. Further processing performed by controller is described in more detail below with respect to FIGS. 2-7. In some variations, the controller (112) and processing performed thereon may be disposed in ECG device (104).

A. Controller

A processing device (108), as depicted in FIG. 1, may comprise a controller (112) in communication with one or more ECG devices (104). The controller (112) may comprise one or more processors and one or more machine-readable memories in communication with the one or more processors. The processor may incorporate data received from memory and operator input to control the processing device (108). The inputs to the controller (112) may be received from one or more machine generated (e.g., ECG devices) and/or human generated sources (e.g., user input). The memory may further store instructions to cause the processor to execute modules, processes and/or functions associated with the processing device, such as the method steps described herein. The controller (112) may be connected to the one or more ECG devices (104) by wired or wireless communication channels. The controller (112) may be configured to control one or more components of the processing device (108) including the network interface (110) and user interface (116).

The controller (112) may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers, or server computing devices such as routing/connectivity components, portable (e.g., hand-held) or laptop devices, multiprocessor systems, microprocessor-based systems, and distributed computing networks. Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

i. Processor

The processor may be any suitable processing device configured to run and/or execute a set of instructions or code and may include one or more data processors, image processors, graphics processing units, physics processing units, digital signal processors, and/or central processing units. The processor may be, for example, a general-purpose processor, Field Programmable Gate Array (FPGA), an Application Specific Integrated Circuit (ASIC), and the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

In some variations, one or more processors may execute the methods described herein in a cloud computing environment or as a Software as a Service (SaaS). For example, at least some of the steps of the methods described herein may be performed by a group of computers in communication via a network (e.g., the Internet) and via one or more appropriate interfaces (e.g., APIs). The cloud computing system may include clients and servers. A client and server are generally remote from each other and typically interact through a communication network. The relationship of client and server arises by virtue of computer programs running on the respective computers and having a client-server relationship to each other.

ii. Memory

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory may store instructions to cause the processor to execute modules, processes and/or functions associated with the processing device (108), such as ECG signal data processing, communication, display, and/or user settings. In some variations, storage may be network-based and accessible for one or more authorized users. Network-based storage may be referred to as remote data storage or cloud data storage. ECG signal data stored in cloud data storage (e.g., database (120)) may be accessible to respective users via a network, such as the Internet. In some variations, database (120) may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, JAVA®, Python, Ruby, VISUAL BASIC®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

B. User Interface

A user interface (116) may permit an operator to interact with and/or control the processing device (108) directly and/or remotely. For example, the user interface (116) may include an input device for an operator to input commands and an output device for an operator and/or other observers to receive output (e.g., view patient data on a display device) related to operation of the processing device (108).

User interface (116) may serve as a communication interface between an operator and the processing device (108). In some variations, the user interface (116) may comprise an input device and output device (e.g., touch screen and display) and be configured to receive input data and output data from one or more of the ECG device (104), computing devices (106, 118, 120, 122), input device, and output device. For example, ECG signal data generated by ECG device (104) may be processed by controller (112) and displayed by the output device (e.g., monitor display). As another example, operator control of an input device (e.g., joystick, keyboard, touch screen) may be received by user interface (116) and then processed by controller (112) for user interface (116) to output a control signal to one or more of the processing device (108) and ECG device (104).

i. Output Device

An output device of a user interface (116) may output ECG signal data corresponding to a subject (102), and may comprise one or more of a display device and audio device. The display device may be configured to display a graphical user interface (GUI) (e.g., GUI as shown in FIG. 8). A display device may permit an operator to view ECG signal data and/or other data processed by the controller (112). In some variations, an output device may comprise a display device including one or more of a light emitting diode (LED), liquid crystal display (LCD), electroluminescent display (ELD), plasma display panel (PDP), thin film transistor (TFT), organic light emitting diodes (OLED), electronic paper/e-ink display, laser display, and holographic display.

An audio device may audibly output subject data, sensor data, system data, alarms and/or warnings. In some variations, an audio device may comprise at least one of a speaker, piezoelectric audio device, magnetostrictive speaker, and/or digital speaker. In some variations, an operator may communicate with other users using the audio device and a communication channel. For example, the operator may form an audio communication channel (e.g., VoIP call) with a remote operator, ECG technician, and/or subject.

ii. Input Device

Some variations of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal.

B. Network Interface

As depicted in FIG. 1, a processing device (108) described herein may communicate with one or more networks (105) and computing devices (118, 120, 122) through a network interface (110). In some variations, the processing device (108) may be in communication with other devices via one or more wired and/or wireless networks. For example, the network interface (110) may permit the processing device (108) to communicate with one or more of a network (105) (e.g., Internet), remote server (122), and database (120). The network interface (110) may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface (110) may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet Message Access Protocol (IMAP) and/or Post Office Protocol (POP)), instant messaging (e.g., eXtensible Messaging and Presence Protocol (XMPP), Session Initiation Protocol for Instant Messaging and Presence Leveraging Extensions (SIMPLE), and/or Instant Messaging and Presence Service (IMPS)), and/or Short Message Service (SMS), or any other suitable communication protocol. Some wireless network deployments combine networks from multiple cellular networks or use a mix of cellular, Wi-Fi, and satellite communication. In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

Processing of the ECG signal data or recording may be performed using the hardware described herein using a wired or wireless communication link with the ECG device coupled to the patient or to the subject. The communication between the processor and the ECG device may or may not be performed in real-time as the ECG signal is received or recorded. The processor may be located in the same housing as the ECG device, or in a separate housing in the same room or building as the ECG device. The processor may also be located in a remote location from the ECG device (e.g., a different building, city, country).

II. Methods

Methods for characterizing an ECG signal are also described here. Generally, methods described here comprise receiving an ECG signal generated by an ECG device and determining ECG signal characteristics based on a set of evaluable multi-beat sequences from the ECG signal. The methods described herein may provide improved precision and accuracy in QTc measurement, as well as in other common ECG-based measurement (e.g., QRS and PR), by determining one or more evaluable multi-beat sequences, thus enabling a reduction of the sample size or in the risk of false positive or other incorrect results relative to cardiac safety assessment in drug development. For instance, improved precision and accuracy may be utilized in late phase trials to avoid a subject being inadvertently excluded from studies due to QT/QTc interval prolongation that incorrectly indicates that the subject is above an exclusion threshold, or to minimize incorrect assessments about the effect of a drug being tested on ECG-based intervals.

The methods described herein provide a stability metric that identifies, for example, the three best consecutive beats for a given sequence of consecutive cardiac beats. The overall precision of the measurement is improved by reducing or minimizing the variability around the measurements. By contrast, the selection of the three best consecutive beats using conventional techniques does not rely on the quantitative assessment of every possible three beat combination.

In some variations, the methods analyze large volumes of ECG data to generate a cardiac safety profile from a standard Phase I study or other clinical or pre-clinical study. The techniques disclosed herein may be applied to patient population studies as well as healthy normal studies, although more eligible patients are likely needed in patient population studies but are often more difficult to recruit as compared to healthy volunteer studies. In some variations, the methods may analyze data from Phase II and III trials to more optimally assess whether a studied drug is causing adverse or potentially dangerous effects on particular study subjects, or to more accurately assess which subjects should be included, excluded, and/or discontinued from a trial based on certain ECG-based parameters.

Figure 2:
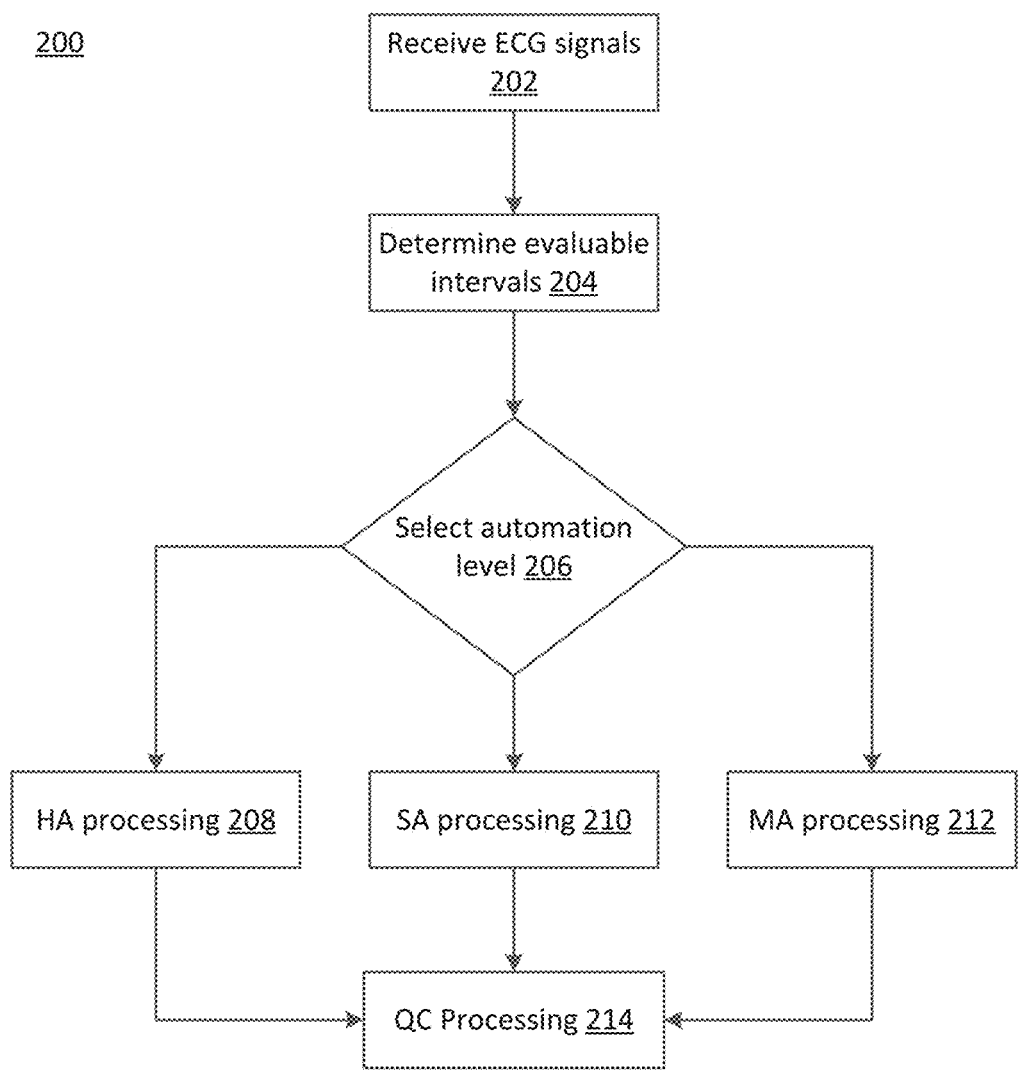
FIG. 2 depicts one variation of a flowchart of an overview of ECG processing.

FIG. 2 depicts one variation of a flowchart to characterize an ECG signal (200). For the sake of example, the ECG signal analysis described with respect to FIG. 2 is based on the ECG parameters of QT, PR, and QRS. The process (200) may begin with receiving the ECG signal(s) generated by an ECG device coupled to a patient or a healthy subject (202). In some variations, the ECG signal data may be received in parallel and/or serially from a plurality of ECG devices, patients, data formats, clinical site locations, and studies, and at different times over a study period. In some variations, the ECG signal data may be pre-processed (e.g., to remove noise). The ECG signal may be processed to generate a set of evaluable intervals (204). In some variations, the set of evaluable intervals is determined based on a signal-to-noise ratio (SNR) comprising a repolarization signal and an isoelectric line as described further in FIG. 3A.

Next, an automation level may be selected (206) from at least one of highly-automated process (HA) (208), semi-automated process (SA) (210) and manual adjudication (MA) (212). The selection of the automation level may be set by the user, or selected or recommended by the processor based upon the initial analysis of the ECG signal. In some variations, the automation level may be selected based on the number and/or quality of one or more ECG intervals that satisfy certain predetermined criteria. In another variation, the set evaluable multi-beat sequences are provided for a particular processing level (e.g., SA). Finally, the results from at least one of HA (208), SA (210) and MA (212) processes may optionally undergo quality control process (214).

Figure 3A:
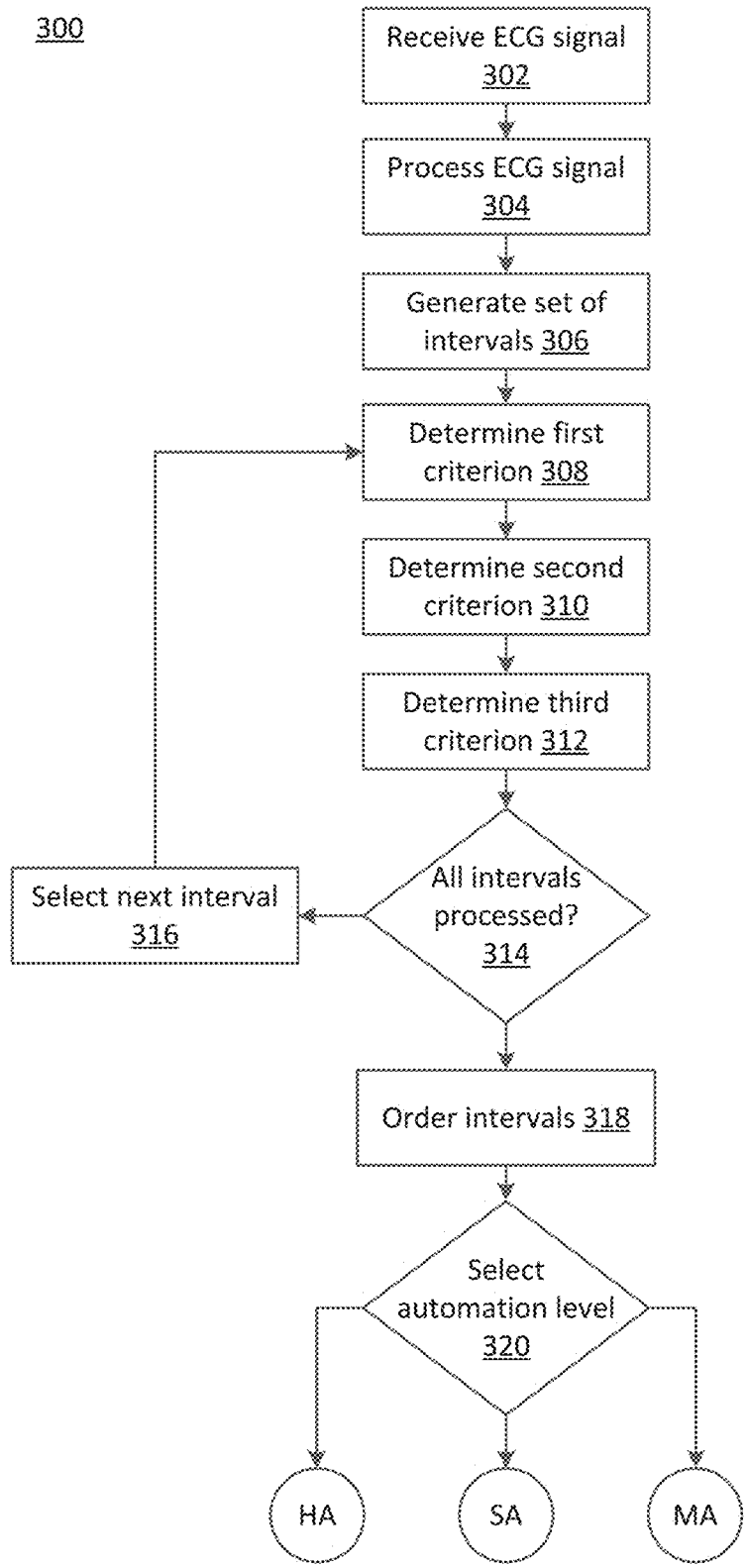
FIG. 3A depicts another variation of a flowchart of ECG processing.

FIG. 3A depicts another variation of a flowchart of ECG processing (300). The process (300) may begin with receiving the ECG signal(s) generated by an ECG device coupled to a patient (302). In some variations, the ECG signal may be processed to de-noise the signal and may include at least one of baseline removal, $^{50}\!/_{60}$ Hz removal and other digital filtering (304). For example, wandering baseline correction, often the result of various movement artifacts from respiration, body movement or exercise, may be performed using highpass filter of about 0.5 Hz to about 1 Hz, or about 0.05 Hz to about 2 Hz, or a time-variant frequency cut-off function based upon the heart rate or RR interval. In still other examples, curve-fitting to the QRS complexes or PQ interval may be performed and a sloped-based correction may be used. EMG correction may be performed using a band-pass filter with a cut-off frequency in the range of about 40 Hz to about 2 kHz, or about 60 Hz to about 1 kHz, for example. A notch filter at about 50 Hz or about 60 Hz may be used to remove electrical interference from power lines. From the continuous ECG signal, a plurality of ECG epochs may be generated around the study time points. The ECG epoch may then be processed to generate a set of replicates of a predetermined length (306). For example, each replicate may have a length of about 10 seconds. In some variations, the epoch having a duration of approximately 10 seconds may comprise one or more replicates comprising a plurality of cardiac beats.

In some variations, processing and ranking of the replicates of one or more epochs may use criteria including stability, signal-to-noise, and abnormal ranges. Each of a first criterion, second criterion, and third criterion may be determined (308, 310, 312). A first criterion may correspond to stability and may be determined using heart rate stability and beat stability. Heart rate stability may be determined based on a median RR value for a predetermined duration prior to each cardiac beat. In some variations, the predetermined duration may be about three minutes. In some variations, the predetermined duration may be in the range of a length of two or more cardiac beats to about 5 minutes. In other variations, the predetermined duration may be in the range of about 30 seconds to about 5 minutes. In some variations, the cardiac beat may be considered stable when the current RR value is within about 15% to about 25% variation of the median RR value or about 10% of the median RR value. Beat stability may be defined as one or more cardiac beat within the replicate not being a normal sinus beat. In some variations, the first criterion may be satisfied and given a value of one when one or both of the heart rate stability and beat stability is satisfied, and is otherwise given a value of zero.

A second criterion may correspond to signal-to-noise of a replicate. When an SNR is not determinable (e.g., unavailable) for reasons such as a fiducial point required for its computation is not detected, then the second criterion is not met. In some variations, the SNR may be determined for each cardiac beat using a repolarization signal and an isoelectric line. In particular, the SNR quantifies the noise components of the repolarization signal (e.g., T-wave) in reference to the components of the isoelectric line evaluated in the PR interval. The isoelectric line represents the level of the ECG signal of the PR interval when the sum of the voltage gradients across the heart equals zero voltage.

In some variations, the SNR may be determined from the unprocessed received ECG signal using all available leads for each cardiac beat. In some variations, the SNR determination may exclude non-sinus beats, but in other variations, non-sinus beats may be included in the SNR determination, or may be determined separately. In other variations, the SNR may correspond to the ratio of the root mean square voltage within a window located inside the QT interval to the root mean square voltage computed from the PR interval. In particular, SNR for each beat may be determined as follows:

$$SNR = 20 * \log\left(\frac{V_{rms}\text{signal}}{V_{rms}\text{noise}}\right), \text{ where } V_{rms} = \frac{1}{n}\sqrt{\sum_{i=1}^{n}(v_i)^2},$$

where n is a $V_{rms}$ interval and v is voltage.

Figure 10:
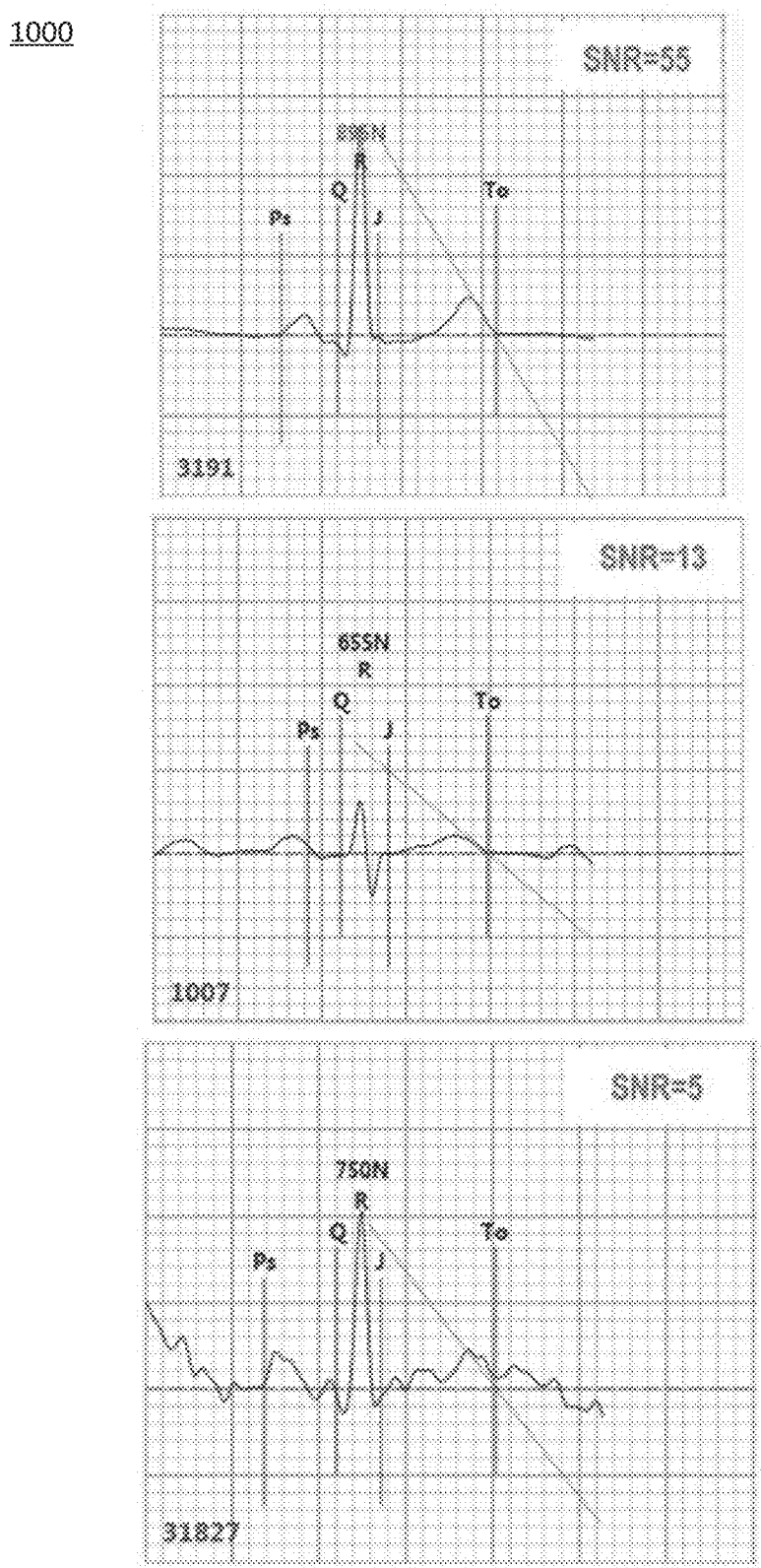
FIG. 10 depicts one variation of a graph of ECG signal data of different SNR.

In some variations, the signal is a root mean square voltage in the T-wave from a J-point until a 4/7RR point and $V_{rms}$ noise is a root mean square voltage in an isoelectric region over a 40 ms interval prior to Q-onset. The 4/7RR point may correspond to an end of the repolarization interval, which may not coincide with the end of the T-wave in scalar leads. The SNR values calculated using the above formula may vary within a positive range, dependent upon the ECG signal quality. In some variations, the SNR may have a range between about 2 and about 60, about 1 and about 45, and about 25 and about 60. Higher SNR corresponds to a higher quality signal. FIG. 10 is a graph (1000) of ECG signal data of different SNR.

In some variations, the end of a T-wave may be determined based upon a 5/7RR point, or depend on the location of the onset of a P-wave on the next cardiac beat, and the isoelectric region may be a region of fixed duration between about 30 ms and 60 ms interval preceding Q-onset or a variable duration based upon the preceding T-wave duration used for the T-wave root mean square voltage. This SNR may be associated with an amplitude of the T-wave in that when the T-wave signal is strong, the value of the SNR is higher regardless of the noise level within the ECG signal. This characteristic increases the likelihood of rejecting cardiac beats from the SNR associated with low T-wave amplitude. Thus, for each beat in a replicate or sequence, the SNR may either be undeterminable or have zero or positive value. Each cardiac beat with a positive SNR is assigned a value of 0, while each beat that is indeterminable or has a SNR of zero is assigned a value of 1. The cardiac beats in each replicate are then totaled, to provide a replicate SNR value.

A third criterion may correspond to abnormal ranges for a replicate or sequence based on a QTcF measurement or other QT metric to be within a predetermined range (physiological range). For example, the range of QTcF may be between about 250 ms and about 750 ms, or between about 300 ms and about 900 ms. A QTcF measurement outside the predetermined range may indicate a failure to measure the QT interval. Each cardiac beat in a replicate with a QTcF outside of the predetermined range or otherwise indeterminable may be assigned a value of one, while those within the predetermined range may be assigned a value of zero. The third criterion may be calculated for each replicate as the total count of values for each cardiac beat in the replicate.

The three criteria may be applied and evaluated on successive non-redundant replicates (314) one by one (316) until all are processed for the entire ECG signal or selected epoch. In some variations, the values of the three criteria may be summed for each replicate while in other variations, the value of each criteria may be weighted before summing. The replicates may be ordered (e.g., ranked) (318) into the set of evaluable replicates or multi-beat sequences using the summed criteria values. In some variations of replicate ranking, the replicates may be sorted from minimum to maximum in the order of the number of intra-replicate beats meeting the criteria. From the available set of replicates, a subset of the best replicates may be determined based upon the total replicate score (e.g., the ten replicates with the lowest criteria scores) and subsequently re-ordered using the total SNR value for each replicate. A second subset of the first subset may be generated based upon the best total SNR values (e.g., three of the ten replicates having the lowest total SNR score) for further processing (e.g., semi-automatic process, highly automatic process). High quality QT interval measurements may thus be determined by utilizing an ordered set of replicates, rather than the entire ECG signal or epoch. Additionally or alternatively, low quality interval measurements may be excluded and reduce the frequency of skewed and/or inconclusive patient results and inconclusive results.

In some variations, the automation level may depend upon the replicate SNR value for the first or second subset, or other SNR value based upon the entire ECG signal or selected epoch, or differences. For example, a difference between the SNR values may reflect the degree of heterogeneity within the different subsets or between the subsets and the entire ECG signal or selected epoch.

Figure 3B:
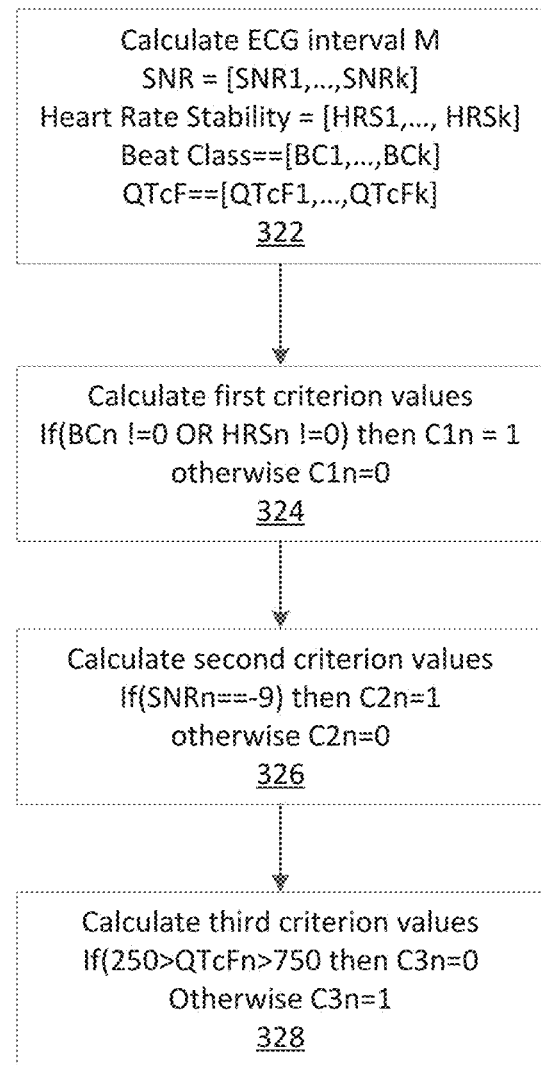
FIG. 3B is a detailed flowchart variation of FIG. 3A.

FIG. 3B is a detailed flowchart variation of a replicate ordering process (318). For a given ECG replicate M, the values of SNR, heart rate stability, beat type (non-sinus beat) and QTcF may be determined (322) for k beats where k is the number of cardiac beats within a replicate.

A first criterion (e.g., stability) value may be calculated (324) where if the beat n is non-sinus or abnormal or the heart rate is unstable (BCn !=0 OR HRSn !=0), then the value of a first criterion count value C1n is 1 and is otherwise 0. C1n represents the count value of beat n for the first criterion. A second criterion (e.g., signal to noise criterion) value may be calculated (326) where if the SNR for the beat is unavailable (SNRn==−9), then a second criterion count value C2n is 1 and is otherwise 0. C2n represents the count value of beat n for the second criterion. A third criterion (e.g., abnormal ranges criterion) value may be calculated (328) where if the QTcF for the beat is between about 250 ms and about 750 ms (e.g., 250 ms>QTcFn>750 ms), then the value of a third criterion count value C3n is 1 and is otherwise 0. C3n represents the count value of beat n for the third criterion.

The table in FIG. 3B provides an example of criterion count values and a sum of criterions C1, C2 and C3 for all beats k of a replicate M. The sum within each of C1, C2 and C3 may be classified into a respective Class 1, Class 2, and Class 3. The replicate may then be ranked in ascending order of Class 1, Class 2, and Class 3. From this ranked set of replicates, non-overlapping replicates may be extracted as the set of evaluable replicates (318). Conversely, the ranked set of replicates may also be used to determine a set of non-evaluable intervals based on one or more of a number of abnormal cardiac beats, unstable heart rate, unavailable SNR, and QTcF exceeding predetermined thresholds. The exemplary scoring system described herein classifies replicates or sequences with the lowest scores as the highest quality, while replicates with higher scores are classified as lower quality. Alternatively, the scoring system may be configured differently such that the replicates or sequences with the highest scores may be classified as high quality while lower scores may be classified as low quality.

Figure 4:
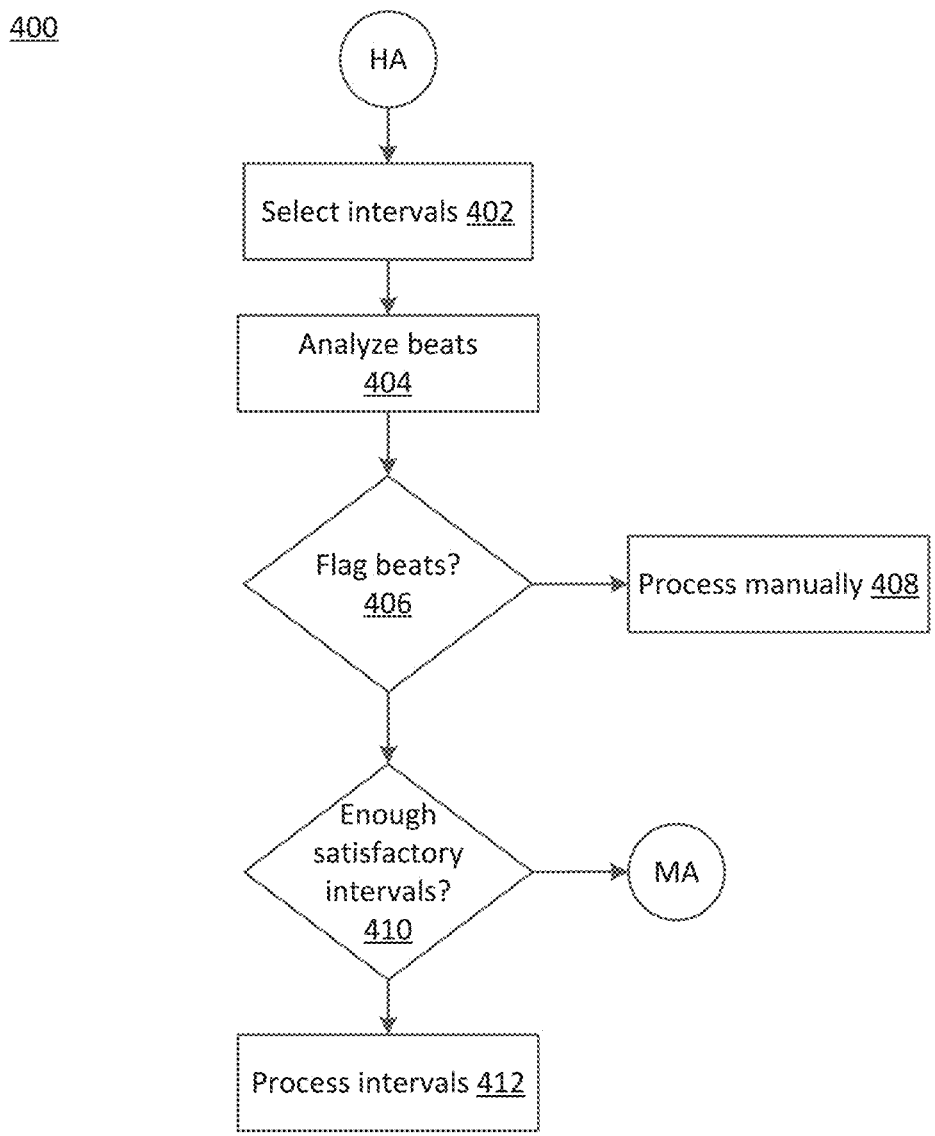
FIG. 4 depicts one variation of a flowchart of highly-automated ECG processing.
Figure 5:
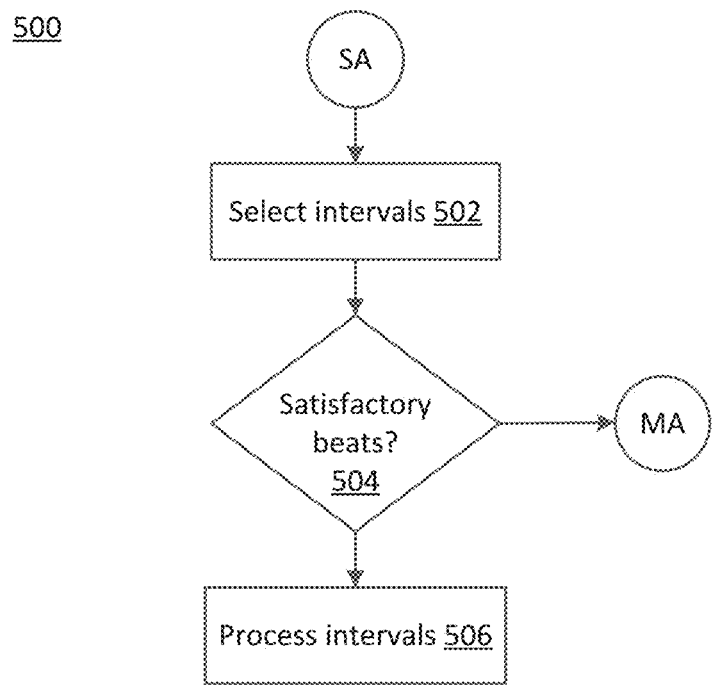
FIG. 5 depicts one variation of a flowchart of semi-automated ECG processing.

After ordering the replicates (318), one or more processing automation levels of the replicates may be selected (320). The ECG signal characteristics may be determined based on the type of processing performed. HA processing may select a predetermined number of replicates for processing (FIG. 4). In some variations, the ten best replicates based on SNR are provided for HA processing. (FIG. 5). In some variations, the three best replicates based on SNR are provided for SA processing. In MA processing (FIG. 6), each replicate may be manually adjudicated by an ECG expert. In some variations, replicates selected for HA and SA processing may be redirected to MA processing if predetermined criteria are not met.

FIG. 4 depicts one variation of highly-automated ECG processing (400). HA processing may classify beats for one of automatic processing and expert review. A predetermined number (e.g., ten) of the best replicates based on SNR may be selected (402). The beats in the set of selected replicates may be automatically analyzed against a set of HA criteria (404). In some variations, the HA analysis criteria may comprise one or more of RR, QTcF, heart rate variability, QTcF variability, ΔRR, and ΔQTcF. RR and QTcF may be checked against a predetermined normal range. Heart rate variability may correspond to a standard deviation of the RR measurements from a replicate with all possible pairs of consecutive beats. QTcF variability may correspond to a standard deviation of QTcF values for a replicate with all beats excluding QT measurement failure. ΔRR may correspond to a percent change of RR value on a beat-to-beat basis exceeding a normal value. ΔQTcF may correspond to a percent change of QTcF value on a beat-to-beat basis exceeding a normal value.

Beats that do not meet the HA criteria may be flagged (406) to determine acceptance or rejection by human expert review (408). In determining if there are enough satisfactory beats (410), the epoch may be directed to MA if there are less than a predetermined number of satisfactory beats. In some variations, if only two replicates or less of the ten replicates are accepted, then the epoch is directed to manual review (MA). Otherwise, the replicate may be automatically processed (412) to select ECG measurements including, but not limited to, RR, PR, QRS and QTcF measurements. The resulting interval measurements from the HA and SA may be stored in memory for further comparison.

Figure 6:
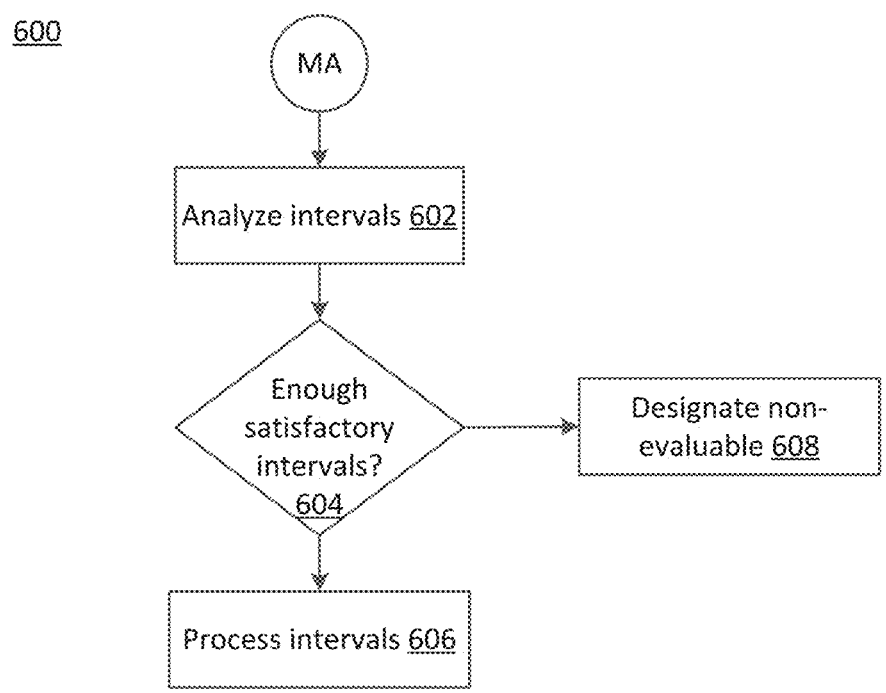
FIG. 6 depicts one variation of a flowchart of manually adjudicated ECG processing.

FIG. 5 depicts one variation of a flowchart of semi-automated (SA) ECG processing (500). A multi-beat sequence (MBS) of the best beats (e.g., three) based on SNR may be selected and analyzed (502). If a sufficient number of the selected beats are determined as satisfactory by human evaluation (504), then the replicates may be processed (506). Otherwise, the replicates may be directed towards manual adjudication review (MA) (FIG. 6). In some variations, if at least three consecutive beats in at least two of the three selected replicates are determined as satisfactory by human evaluation, then the replicates may be processed (506) by performing interval measurements comprising RR, PR, QRS, and QTcF measurements.

FIG. 6 depicts one variation of a flowchart of manually adjudicated ECG processing (600). Each interval may be analyzed by manual adjudication to extract at least three beats with full fiducial correction (602) or confirmation. If there are enough satisfactory measurements (604), then the accepted beats may be processed (606) by performing measurements comprising RR, PR, QRS, and QTcF and calculating statistics comprising the means and medians. In some variations, if there are at least three acceptable beats in at least three replicates, then the epoch may be deemed acceptable. An epoch may be designated as non-evaluable (608) if there is less than a predetermined number of accepted/corrected beats and replicates. In some variations, a non-evaluable epoch includes less than three accepted/corrected beats and less than three accepted/corrected replicates.

Figure 7:
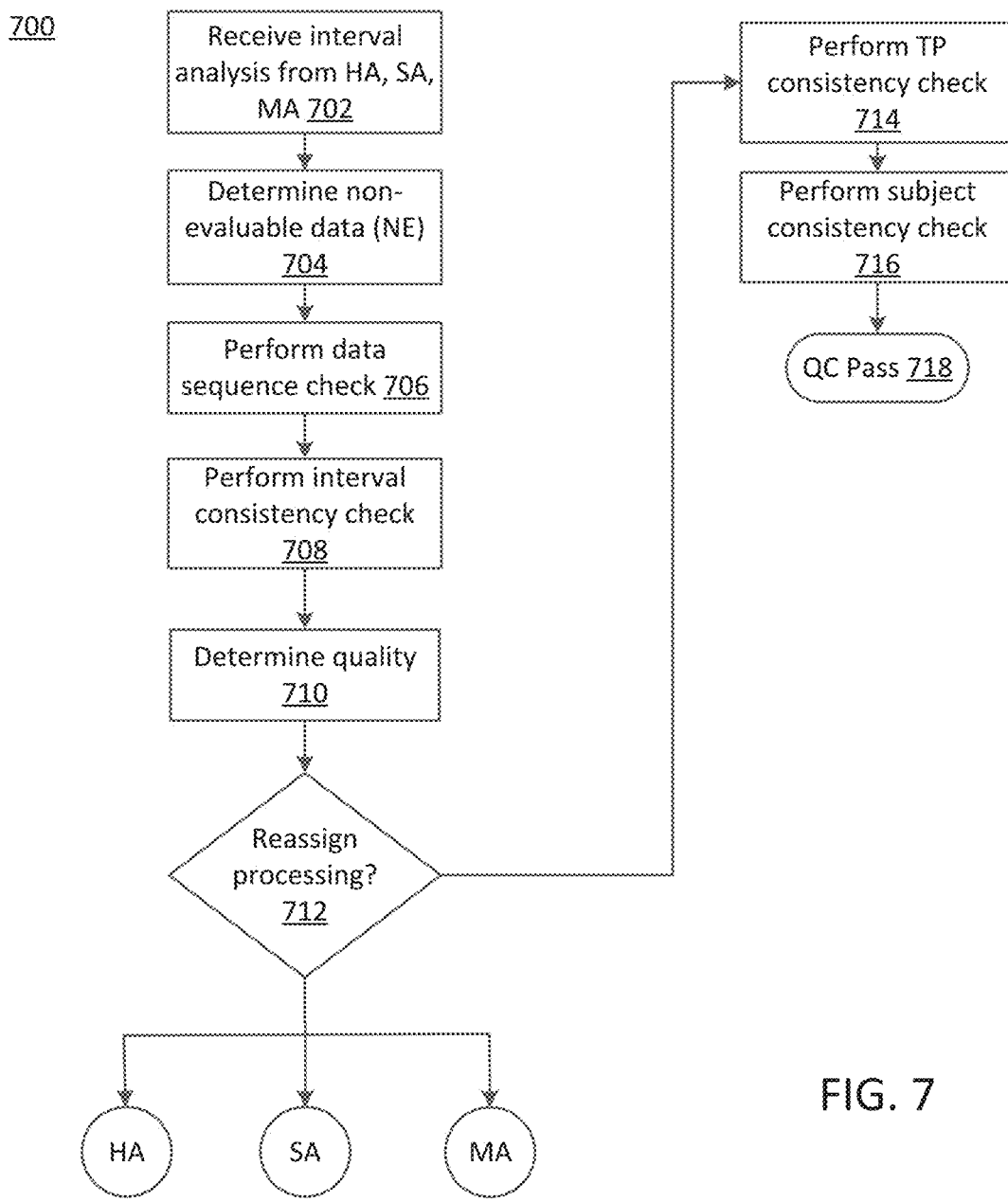
FIG. 7 depicts one variation of a flowchart of ECG quality control processing.

FIG. 7 depicts one variation of a flowchart of ECG quality control processing (700) that may verify results where quality control has not been provided before. After performing one or more of HA, SA, and MA processing, a quality control process may be performed based on the extracted interval measurements to review the quality of the measurements. The measurements and analysis performed by HA, SA, and MA processing may be received (702) for human review of the overall dataset to identify missing data and non-evaluable (NE) data (704). Missing intervals may be identified and sent for human review. Where the quality of the data is unsatisfactory, the replicates may be sent for MA processing. Based on the quality classification of the replicates, a determination of processing reassignment may be performed (712). For HA processed replicates, if less than a predetermined number of beats are classified as accepted for a given epoch, then the overall epoch may be reassigned for MA processing. For an SA processed replicate, if there are not enough cardiac beats that are accepted, based on the MBS requirement, then the epoch may be reassigned to repeat SA processing, and subsequently for MA processing if necessary. For example, if the reassigned SA processing is unable to identify three accepted consecutive cardiac beats (MBS), then MA processing is performed. For MA processing, if less than a predetermined number of cardiac beats are accepted, then the epoch may be reassigned for MA processing with human review performed by another reviewer such as a more senior reviewer. A study-based data sequence check may be performed (706) to review for errors such as duplicates and missing time points. The overall data set from the study may be ordered using the time stamp of the replicates. The time point associated with each replicate may be reviewed and then manually corrected. Next, a replicate interval consistency check may be performed (708) to identify discrepancies between measurements. These checking steps may be automated or manually performed. In some variations, QTcF interval measurements from HA and SA processing may be compared to identify discrepancies between the replicates measurements. Replicate intervals with a discrepancy may be sent for MA processing. The quality of each interval may then be determined (710) based on the replicates measurement criteria in Table 1 in order to classify the replicates as either accepted or rejected where HA and SA processing includes differing criteria as noted in the process column.

TABLE 1

| Interval Flagging | Parameter | Process | Exemplary Starting Threshold(s) |
|---|---|---|---|
| Intra-Epoch Standard Deviation | HR | MA/HA | >8, 12, 14, 16, 20 |
| | QTcF/QTcI | MA/HA | >15 |
| | PR | MA/SA | >15 |
| | QRS | MA/SA | >5 |
| Difference from TP Median | QTcF/QTcI | MA/HA | >15 |
| | PR | MA/SA | >15 |
| | QRS | MA/SA | >6 |

TABLE 1-continued

| Interval Flagging | Parameter | Process | Exemplary Starting Threshold(s) |
|---|---|---|---|
| Additional Outlier Identification | HR | MA/HA | (>1.5 × IQR + Q3 OR <1.5 × IQR − Q1) AND TP Range >10 |
| | QTcF/QTcI | MA/HA | (>1.5 × IQR + Q3 OR <1.5 × IQR − Q1) AND TP epoch Range >10 |
| | PR | MA/SA | (>1.5 × IQR + Q3 OR <1.5 × IQR − Q1) AND TP epoch Range >10 |
| | QRS | MA/SA | (>1.5 × IQR + Q3 OR <1.5 × IQR − Q1) AND TP epoch Range >10 |

Based on the quality classification of the replicates, a determination of processing reassignment may be performed (712). For HA processed replicates, if less than a predetermined number of intervals beats are classified as accepted for a given TP epoch, then the overall TP epoch may be reassigned for MA processing. For SA processed replicates, if not enough cardiac beats are accepted, based on the MBS criteria, then any of a predetermined number of intervals (e.g., three) are not accepted, the epoch TP may be reassigned to repeat SA processing, and subsequently for MA processing if necessary. For example, if the reassigned SA processing is unable to identify three accepted cardiac beats (MBS), then MA processing may be performed. For MA processing, if less than a predetermined number of cardiac beats are accepted, then the epoch TP may be reassigned for MA processing with human review performed by a more senior reviewer.

If no reassignment processing is performed, then an epoch TP consistency check may be performed (714) based on the replicate measurement stability criteria in Table 2 to classify the intervals on an epoch TP basis as either accepted or rejected, where HA and SA processing may include differing criteria as noted in the process column. Rejected epoch TPs may be directed towards MA processing.

TABLE 2

| Time Point Flagging | Parameter | Process | Starting Threshold |
|---|---|---|---|
| Absolute Value | HR | MA/HA | <40 OR >100 |
| | QTcF/QTcI | MA/SA | <355 OR >455 |
| | PR | MA/SA | <100 OR >200 |
| | QRS | MA/HA | <90 OR >120 |
| Time Point Range | HR | MA/HA | >20 |
| | QTcF/QTcI | MA/SA | >20 |
| | PR | MA/SA | >20 |
| | QRS | MA/HA | >8 |

Although the foregoing invention has, for the purposes of clarity and understanding been described in some detail by way of illustration and example, it will be apparent that certain changes and modifications may be practiced, and are intended to fall within the scope of the appended claims. Additionally, it should be appreciated that the devices described here may comprise any combination of device components and features described above.

We claim:

1. A method of providing interval measurements based on an electrocardiogram (ECG) signal comprising:
   receiving an ECG signal generated by an ECG device coupled to a subject, wherein the ECG signal generated by the ECG device comprises a plurality of cardiac beats;
   determining, by a computer processor, a signal-to-noise ratio (SNR) for each cardiac beat based on a repolarization signal and an isoelectric line;
   identifying a set of evaluable multi-beat sequences using the SNR of each cardiac beat, wherein the sequences have a pre-determined length; and
   determining, by a computer processor, the interval measurements from the set of evaluable multi-beat sequences.

2. The method of claim 1, wherein the repolarization signal corresponds to a T-wave voltage and the isoelectric line corresponds to an ECG voltage level of a PR interval where a sum of voltage gradients is zero.

3. The method of claim 1, wherein identifying the set of evaluable multi-beat sequences excludes multi-beat sequences that include non-sinus origin.

4. The method of claim 1, wherein the SNR is based upon a ratio of a root mean square voltage of a T-wave and a root mean square voltage of an isoelectric region prior to Q-onset of a corresponding QRS complex to the T-wave.

5. The method of claim 1, wherein the pre-determined length is a pre-determined set length or a pre-determined minimum length.

6. The method of claim 5, wherein the length is a time duration or several cardiac beats.

7. The method of claim 1, wherein the SNR is $$SNR = 20 * \log\left(\frac{V_{rms}\text{signal}}{V_{rms}\text{noise}}\right) \text{ where } V_{rms} = \sqrt{\frac{1}{n} * \sum_{i=1}^{n} (v_i)^2}$$

and n is a $V_{rms}$ interval and v is voltage.

8. The method of claim 7, wherein the $V_{rms}$ signal is a root mean square voltage in the T-wave from a J-point until a 4/7RR point and $V_{rms}$ noise is a root mean square voltage in an isoelectric region over a 40 ms interval prior to Q-onset.

9. The method of claim 1, wherein determining the set of evaluable multi-beat sequences is based on beat characteristics comprising at least one of heart rate stability, non-sinus beat morphology and QTcF.

10. The method of claim 9, wherein the heart rate stability is based on a median RR value for a predetermined duration prior to each cardiac beat, and wherein the beat excluded from the set of evaluable multi-beat sequences when current RR value is greater than 20% of the median RR value.

11. The method of claim 1, wherein determining the set of evaluable multi-beat sequences comprises determining an order of the multi-beat sequences in the ECG signal based on at least one of a number of beats within the multi-beat sequence, heart rate stability, non-sinus beat morphology, the SNR, and a QTcF.

12. The method of claim 1, further comprising selecting a processing automation level from a plurality of processing automation levels, wherein determining the interval measurements is based on the selected processing automation level.

13. The method of claim 12, wherein the plurality of automation levels comprises a highly automatic level, a semi-automatic level and a manual adjudication level, wherein the semi-automatic level includes greater user input than the highly automatic level, and the manual adjudication level requires greater user input than the semi-automatic level.

14. The method of claim 13, wherein the highly automatic level comprises classifying beats for one of automatic processing and human review.

15. The method of claim 13, wherein the semi-automatic level is selected when at least three consecutive beats in at least two of three sequences of a pre-determined length in the set of multi-beat sequences are determined as satisfactory.

16. The method of claim 13, wherein the manual adjudication level comprises determining the interval measurements based on extraction of at least three consecutive beats with full fiducial correction.

17. The method of claim 1, further comprising removing noise from the ECG signal comprising at least one of baseline removal and 60 Hz interference removal.

18. The method of claim 1, further comprising performing a consistency check of the interval measurements, wherein the consistency check comprises at least one of a data sequence check, an interval measurement comparison and time point check.

19. The method of claim 1, further comprising selecting a set of evaluable replicates for a QT evaluation with a new chemical entity.

20. The method of claim 19, wherein the QT evaluation is performed for a Thorough QT (TQT) study, an exploratory Investigation New Drug study, a First-In-Human study, a microdose study, phase I study, phase II study or a phase III study.

21. A system for providing interval measurements based on an electrocardiogram (ECG) signal, comprising the system comprising:
   a receiver to receive an ECG signal generated by an ECG device coupled to a patient, wherein the ECG signal generated by the ECG device comprises a plurality of cardiac beats; and
   a processor configured to determine a signal-to-noise ratio (SNR) for each cardiac beat based on a repolarization signal and an isoelectric line;
   a processor configured to identify a set of evaluable multi-beat sequences using the SNR of each cardiac beat, wherein the sequences have a pre-determined length; and
   a processor configured to determine the interval measurement from the set of evaluable multi-beat sequences.

22. The system of claim 21, wherein the repolarization signal corresponds to a T-wave voltage and the isoelectric line corresponds to an ECG voltage level of a PR interval where a sum of voltage gradients is zero.

23. The system of claim 21, wherein identifying the set of evaluable multi-beat sequences excludes multi-beat sequences that include non-sinus origin.

24. The system of claim 21, wherein the SNR is based upon a ratio of a root mean square voltage of a T-wave and a root mean square voltage of an isoelectric region prior to Q-onset of a corresponding QRS complex to the T-wave.

25. The system of claim 21, wherein the pre-determined length is a pre-determined set length or a pre-determined minimum length.

26. The system of claim 25, wherein the length is a time duration or several cardiac beats.

27. The system of claim 21, wherein the SNR is $$SNR = 20 * \log\left(\frac{V_{rms}\text{signal}}{V_{rms}\text{noise}}\right) \text{ where } V_{rms} = \sqrt{\frac{1}{n} * \sum_{i=1}^{n} (v_i)^2}$$

and n is a $V_{rms}$ interval and v is voltage.

28. The system of claim 27, wherein the $V_{rms}$ signal is a root mean square voltage in the T-wave from a J-point until a 4/7RR point and $V_{rms}$ noise is a root mean square voltage in an isoelectric region over a 40 ms interval prior to Q-onset.

* * * * *